United States Patent [19]

Young

[11] 4,152,272

[45] May 1, 1979

[54] FABRIC CONDITIONING COMPOSITION

[75] Inventor: Kenneth Young, Whitley Bay, England

[73] Assignee: The Procter & Gamble Company, Cincinnati, Ohio

[21] Appl. No.: 845,090

[22] Filed: Oct. 25, 1977

[30] Foreign Application Priority Data

Oct. 29, 1976 [GB] United Kingdom .............. 45078/76

[51] Int. Cl.$^2$ ........................................... D06M 13/46
[52] U.S. Cl. ....................................... 252/8.8; 8/137; 252/8.6; 252/522
[58] Field of Search ..................... 252/8.8, 8.6; 8/522, 8/137

[56] References Cited

U.S. PATENT DOCUMENTS

| | | | |
|---|---|---|---|
| 3,137,631 | 6/1964 | Soloway | 424/16 |
| 3,856,699 | 12/1974 | Miyano et al. | 252/522 |
| 3,936,537 | 2/1976 | Baskerville et al. | 252/8.8 |
| 3,936,538 | 2/1976 | Marshall et al. | 252/8.8 |
| 4,012,326 | 3/1977 | Rudy et al. | 252/8.8 |
| 4,051,159 | 9/1977 | Tsoucalas et al. | 252/522 |
| 4,067,824 | 1/1978 | Teng et al. | 252/522 |

*Primary Examiner*—William E. Schulz

[57] ABSTRACT

Fabric conditioning compositions contain particles of size 0.1 to 200 microns and of melting point 38° C. to 150° C. and comprising a wax-like carrier substance and a perfume. The particles are distributed throughout a composition, especially an aqueous fabric-softening composition, which contains a fabric-substantive cationic surfactant.

11 Claims, No Drawings

FABRIC CONDITIONING COMPOSITION

BACKGROUND OF THE INVENTION

The present invention relates to perfumed conditioning compositions suitable for applying to fabrics in a rinse or like treatment.

In the past, most domestic detergent compositions and rinse-added textile softeners have been perfumed, but in general little of the perfume is transmitted to the fabrics, except when special fabric-substantive perfumes are used, as described in British Pat. No. 838,240.

The German Offenlegungsschrift No. 26 31 129 describes textile treatment compositions containing prills of size 5 to 2000 microns comprising 95 to 99.5% of a fabric softening (and antistatic) agent and 0.5 to 5% of a non-fabric softening fabric conditioning material, e.g. a perfume. Such prills are entrained and carried with the fabrics into a fabric dryer where they melt or soften at the temperature reached in the dryer. The melting of the prills allows the fabric softening agent to spread over the fabric surfaces by virtue of the tumbling action of the dryer and further causes the non-fabric softening agent to deposit efficiently on to the fabrics being dried.

The German Offenlegungsschrift No. 27 02 162 describes fabric conditioning particles of size from 5 to 2000 microns comprising 20–53% castor wax, 45–80% quaternary fabric softener and optionally from 0.1 to 2% perfume. They are intended to be dispersed in detergent compositions. British Patent 1,204,123 describes mixtures of perfumes—other things in an extrudable solid, which mixtures are formed into granules, which are added to surfactant-containing powders.

It is one object of the present invention to provide compositions which contain perfume and in which the perfume can be more effectively applied to fabrics. The enhanced utilization of perfume enables the use of lower levels with the same or even improved perfume impact.

It is another object of the invention to provide perfume-containing compositions that give greater perfume substantially to fabric treated with aqueous liquors containing the compositions.

SUMMARY OF THE INVENTION

According to the invention, there is provided a perfumed conditioning composition which comprises from 0.1% to 20% by weight of the composition of particles having an average particle size in the range from 0.1 to 200 microns and having a melting point in the range from 38° C. to 150° C. said particles comprising, by weight of the particles, (a) less than 95% and at least 25% of a carrier substance and (b) from 1% to 75% of a perfume, said particles being incorporated into a composition which contains a fabric-substantive cationic surfactant.

The present invention is based on the recognition that perfume-contaning particles, of a defined melting point and size, can be incorporated into a composition containing a fabric-substantive cationic surfactant. It is believed that the cationic surfactant in the composition becomes associated, in use of the composition, with the perfumed particles and assists in carying the particles to a fabric surface where they are retained and subsequently release their perfume, especially during heat treatment such as drying or ironing.

Provided that it contains a fabric-substantive cationic surfactant, the composition can be of any type and in any physical form. However, aqueous rinse-added fabric softening compositions are highly preferred.

DETAILED DESCRIPTION OF THE INVENTION

The particles

It is important that the perfume-containing particles have a specific size range. The useful size range of the particles is limited at the low end by undue loss of perfume from the surface of the particles even before they are melted, as, if the particles are less than about 0.1 microns, their surface area per unit weight becomes too great. On the other hand, if the particles have a dimension greater than about 200 microns, they are not sufficiently susceptible to the action of the cationic surfactant in the remainder of the composition in promoting substantivity. Preferably the size of the particles is in the range from about 1 to 100 microns especially about 10 to 50 microns. This linear dimension for any individual particle represents the length of the longest straight line joining two points on the surface of the particle.

Another critical physical property of the particles used in the present invention is their melting point and it is essential that they melt in the range from 38° C. to 150° C., preferably from 65° C. to 100° C. The melting point of the particles is usually a function of the carrier substance employed but it should be understood that it is the melting point of the particle rather than of the carrier substance that is important.

The carrier substance can be any substantially water-insoluble substance compatible with and miscible with the perfume and harmless or beneficial to the fabrics when dispersed and melted on to them. The mixture of carrier and perfume must have a melting point in the range defined above. The carrier substance is normally a waxy material and a description of waxes is given in the book "Chemistry and Technology of Waxes" A.H. Warth Second Edition, 1960, incorporated herein by reference.

Suitable materials include macro- and microcrystalline hydrocarbon waxes, derived from petroleum or made synthetically, ester waxes such as bees wax, carnauba wax, ozokerite; fatty acid esters of mono- or polyhydric alcohols; hardened fatty acids and hydroxy fatty acids; higher monohydric alcohols. Preferred waxes are the microcrystalline waxes and the Fischer-Tropsch waxes described below.

Some very effective microcrystalline waxes include:
Microcrystalline wax 160/165 sold by Shell Chemicals
Microcrystalline wax 185/190 sold by Shell Chemicals (the numerical ranges are believed to represent the melting point ranges —° F.)
Microcrystalline wax 160/25 Y sold by BP Chemicals
Microcrystalline wax OK239 sold by Astor Chemicals Ltd.
Mobilwax 2305 sold by Mobil Oil Company Limited, and
Mobilwax 2360 sold by Mobil Oil Company Limited
Witcodur 263 Mpt. 83°–89° C. sold by Witco Chemicals (Holland)
Witcodur 272 Mpt. 83°–89° C. sold by Witco Chemicals (Holland)
Witcodur 143 Mpt. 79°–84° C. sold by Witco Chemicals (Holland)
Witcodur 145 Mpt. 78°–83° C. sold by Witco Chemicals (Holland)

Witcodur 146 Mpt. 70°–75° C. sold by Witco Chemicals (Holland)

Fischer Tropsch waxes, such as those sold by Veba Chemie, AG, are also preferred, for example VEBA wax SP 1044 (melting point about 106°–111° C.). Macrocrystalline hydrocarbon waxes, such as high melting paraffin wax, are also useful in the present invention.

A great variety of waxy esters are also suitable. These include the naturally derived ester waxes, preferably those with low saponification value, that is not exceeding 100, preferably below 60. Also suitable, provided that they are chosen as having high enough melting point when mixed with the perfume are fatty acid esters and partial esters of mono-and polyhydric alcohols or anhydrides thereof, said alcohols or anhydrides having 1 to 8 carbon atoms. These substances can themselves be employed as textile softeners in fabric conditioning compositions: in the present invention, they can be present both in the particle as the or part of the carrier substance and in the remainder of the composition as part of the fabric softening component.

These fatty acid esters and partial esters are more fully described in the German Offenlegungsschrift No. 26 31 114. These materials are fatty acid esters of mono- or polyhydric alcohols or anhydrides having from 1 to 8 carbon atoms. It is preferred that the fatty acid ester should have at least 1, more preferably 2, free (i.e. unesterified) hydroxyl groups and at least 1, more preferably at least 2 fatty acyl groups.

The mono- or polyhydric alcohol portion of the ester can be represented by methanol, isobutanol, 2-ethylhexanol, isopropanol, ethylene glycol and polyethylene glycol with a maximum of 5 ethylene glycol units, glycerol, diglycerol, xylitol, erythritol, pentaerythritol, sorbitol or sorbitan. Ethylene glycol, glycerol and sorbitan esters are particularly preferred. The fatty acid portion of the ester normally comprises a fatty acid having from 12 to 22 carbon atoms, typical examples being lauric acid, myristic acid, palmitic acid, stearic acid and behenic acid.

Specific useful fatty acid partial esters are xylitol monopalmitate, pentaerythritol mono-stearate, glycerol monostearate and ethylene glycol monostearate. As with the sorbitan esters, commercially available monoesters normally contain substantial quantities of di- or tri-esters.

Other suitable carrier materials are fatty alcohols of about 16 carbon atoms upwards, such as octadecanol, eicosanol, and tallow alcohols. Higher nearly saturated fatty acids can also be used, for example palmitic, stearic, arachidic, hardened fatty acid from tallow or fish oils, or hydrogenated castor oil (known as castorwax). All these substances are commercially available. A table of physical properties of some common waxes is published in Soap & Chemical Specialties, December 1957, p. 141, and is hereby incorporated by reference.

The particles used in the present invention contain, in addition to the carrier substance, a perfume. So that it is not released too soon, it is preferred that the perfumes or their components do not have boiling points less than about 100° C. and preferably have boiling points in excess of 200° C. However, the particles used in the present invention are also useful in enhancing the residuality on fabrics of perfumes containing more labile components by delaying the release of these components.

The perfume materials which can be used in the fabric conditioning prills of the present invention can be of any odoriferous material and will be selected according to the desires of the formulator. In general terms, such perfume materials are characterized by a vapor pressure below atmospheric pressure at ambient temperatures. The high boiling perfume materials employed herein wwill most often be solids at ambient temperatures, but also can include high boiling liquids. A wide variety of chemicals are known for perfumery uses, including materials such as aldehydes, ketones, esters, and the like. More commonly, naturallyoccuring plant and animal oils and exudates comprising complex mixtures of various chemical components are known for use as perfumes, and such materials can be used herein. The perfumes herein can be relatively simple in their composition, or can comprise highly sophisticated, complex mixtures of natural and synthetic chemical components, all chosen to provide any desired odor.

Typical perfumes herein can comprise, for example the high boiling components of woody/earthy bases containing exotic materials such as sandalwood oil, civet, patchouli oil, and the like. The perfumes herein can be of a light, floral fragrance, e.g., high boiling components of rose extract, violet extract, and the like. The perfumes herein can be formulated to provide desirable fruity odors., e.g., lime, lemon, orange, and the like. In short, the perfume can be any material (of appropriate chemical and physical properties) which exudes a pleasant or otherwise desirable odor when applied to fabrics.

Examples of particularly suitable perfume materials and their boiling points are shown as follows:

| PERFUME | BOILING POINT |
| --- | --- |
| Musk Ambrette | * |
| Musk Ketone | * |
| Musk Tibetene | * |
| Musk Xylol | * |
| Vanillin | 285° C. |
| Ethyl Vanillin | * |
| Aurantiol | * |
| Tonalid | 248° C. |
| Thymol | 233° C. |
| Heliotropine | 263° C. |
| Cinnamyl Cinnamate | 370° C. |
| Benzyl Cinnamate | 228° C.–230° C. at 22 mmHg |
| β-Methyl Napthyl Ketone | 330° C. |
| Trichloromethylphenyl carbinyl Acetate | 282° C. |

*Indicates boiling point or decompositon point in excess of 200° C.

Perfume materials such as these are described more fully in S. Arctander, *Perfume Flavors and Chemicals, Vols. I and II*, Aurthor, Montclair, N.J. and the *Merck Index, 8th Edition*, Merck & Co., Inc. Rahway, N.J., both references being incorporated herein by reference.

Preferred perfume materials include musk ambrette, musk ketone, musk tibetene, musk xylol, aurantiol, ethyl vanillin and mixtures of these perfume materials.

The particles used in the present invention contain less than 95% and at least 25% of the carrier substance and from 1% to 75% of the perfume. Preferably, there is from 50% to 90% of the carrier and from 10% to 40% of the perfume. The melting point of the particles is preferably from 64° C. to 100° C. as determined by a capillary tube method, for instance the method of the American Oil Chemists Association(A.O.C.A.) Cc 1-25, incorporated herein by reference.

Although particles consisting entirely of the above two components are entirely satisfactory, it is also possible to include an additional component or components into the particle. This component may be simply a diluent, but normally it is selected to have some other function. Preferably it consists of a cationic surfactant of any of the types described hereinafter, and serves to improve the affinity of the particles for the fibre surfaces during use of the product. It must be understood that this cationic surfactant component of the particle is additional to the cationic surfactant which must, according to the present invention, be present in the remainder of the composition.

The additional component can also be an absorbent solid such as finely divided silica, clay, starch, etc. Suitable fine silica materials are well known commercially available pyrogenic or fumed silicas, sold under Trade names such as Cabosil (G. L. Cabot Inc.), Aerogel 500 (J. M. Huber Corp.), Syloid 244, −63, −65 (W. R. Grace and Co.), and Li-sil 233 (Pittsburg Plate Glass Co.).

Suitable clay materials include kaolinites and bentonites, as described in British Pat. No. 1,460,646. Preferred are the smectite clays described in British Pat. No. 1,400,898, which have textile softening properties. These are three layer, expandable, clays, such as nontronite, saponite and montmorillonite, volchonskoite, hectorite and sauconite. Such clays are available unde Trade names, for example: Thixogel No. 1 and Gelwhite GP and Soft Dark from Georgia Kaolin Co.; Volclay BC and Volclay No. 325 from American Colloid Co.; Veegum Pro and Veegum F. from T. R. Venderbilt.

Any additional component is usually present in an amount from 10% to 50% by weight of the particles. In the preferred case where the additional component is a cationic surfactant, the ratio of carrier substance to cationic surfactant is preferably at least 3:1, especially from 5:1 to 20:1. These preferred weight ratios help to keep the particle in a homogeneous phase, although such homogeneity is not essential.

As already indicated, the wax/perfume particles of the present invention are incorporated into a liquid or solid composition which itself contains a fabric substantive cationic surfactant.

The Cationic Surfactant

Very many cationic surfactants are known in the art, and almost any cationic surfactant having at least one long chain alkyl group of about 10 to 24 carbon atoms in the molecule is suitable. Numerous such compounds are described in "Cationic Surfactants", Jungermann 1970, the disclosures of which are incorporated herein by reference.

Useful cationic surfactants include compounds selected from:

(i) non-cyclic quaternary ammonium salts having at least one $C_{12-30}$ alkyl chain, (ii) substituted polyamine salts of formula

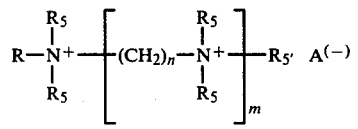

(I)

wherein R is an alkyl or alkenyl group having 10 to 22 carbon atoms, the $R_5$'s which may be the same or different each represent hydrogen, a $(C_2H_4O)_pH$ or $(C_3H_6O)_qH$, or a $C_{1-3}$ alkyl group, where each of p and q may be 0 or a number such that $(p+q)$ does not exceed 25, m is from 1 to 9, n is from 2 to 6, and $A^{(-)}$ represents one or more anions having total charge balancing that of the nitrogen atoms, (iii) $C_{8-25}$ alkyl imidazolinium salts, (iv) $C_{12-20}$ alkyl pyridinium salts, and (v) mixtures of any of these.

Preferred cationic surfactants of class (i) are of the general formula $$R_1 R_2 R_3 R_4 N^+ A^- \quad \text{(II)}$$

wherein groups $R_1$, $R_2$, $R_3$ and $R_4$ are alkyl or substituted alkyl, and one or two of which are alkyl groups with 12 to 30 carbon atoms, and A is an anion, of example chloride, bromide, methyl sulfate, etc.

Specific examples of cationic compounds in this group are: dodecyl trimethyl ammonium bromide, tetradecyl trimethyl ammonium chloride, pentadecyl trimethyl ammonium chloride, cetyl trimethyl ammonium bromide, stearyl trimethyl ammonium bromide, tallow trimethyl ammonium chloride, eicosyl trimethyl ammonium chloride, dodecyl trimethyl ammonium methyl sulphate, tallow trimethyl ammonium acetate and tallow dimethyl benzyl ammonium chloride.

Conventional quaternary ammonium softening agents are preferred ingredients of the compositions of the present invention. These materials have the above formula wherein $R_1$ and $R_2$ are each $C_{12}$-$C_{22}$ fatty alkyl and $R_3$ and $R_4$ are each $C_1$-$C_4$ alkyl. Such softening agent can be used in the present invention in conjunction with the preferred single long chain cationic surfactants.

Some specific examples of quaternary ammonium softening agents are: di dodecyl dimethyl ammonium bromide, di tetradecyl dimethyl ammonium chloride, di pentadecyl dimethyl ammonium chloride, di dodecyl diethyl ammonium chloride, di tetradecyl dipropyl ammonium chloride, di tallow dimethyl ammonium chloride, di tallow dimethyl ammonium methyl sulphate, di tallow diethyl ammonium chloride, di dodecyl diethyl ammonium chloride, di dodecyl diethyl ammonium acetate and di tallow dipropyl ammonium phosphate.

Preferred are ditallow dimethyl ammonium chloride or methyl sulphate.

Also useful in the present invention are substituted polyamine salts, for example compounds of the formula

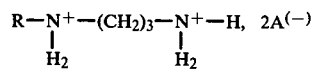

wherein R is a $C_{10}$-$C_{22}$ alkyl or alkenyl group, preferably $C_{16-18}$ alkyl, and A is an anion. In preferred compositions, the N-hydrogen atoms are ethoxylated with up to 25 ethoxy groups in all, preferably with from about 3 to 6 ethoxy groups in all. $A^{(-)}$ may represent a dihalide or any appropriate acidic radical such as the diacetate, or higher saturated or unsaturated acyl groups up to $C_{22}$.

Alkyl imidazolinium salts of class (iii) useful in the present invention are generally believed to have cations of the general formula:

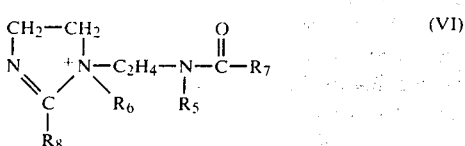

or, more probably,

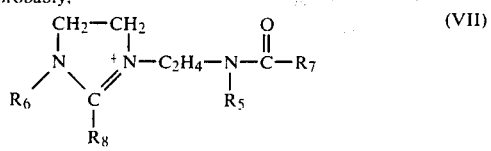

wherein $R_6$ is a $C_1$-$C_4$ alkyl radical, $R_7$ is hydrogen or a $C_1$-$C_{25}$ alkyl radical, $R_8$ is a $C_8$-$C_{25}$ alkyl radical.

A preferred member of this class is believed to have formula VII wherein $R_5$ is H, $R_6$ is methyl, and $R_7$ and $R_8$ are tallow alkyl, and is marketed under the Trade name Varisoft-455 or -475 by Ashland Chemical Company, Ohio, USA. Also suitable are the imidazolinium softeners described in U.S. Pat. application 687,951 filed on July 27, 1976, which application also describes a method of preparing such compounds and is incorporated herein by reference.

Alkyl pyridinium salts of class (iv) useful in the present invention have cations of the general formula:

wherein $R_9$ is a $C_{12}$-$C_{20}$ alkyl radical. A typical useful material of this type is cetyl pyridinium chloride. Also suitable are dodecyl pyridinium bromide, tetradecyl pyridinium chloride, stearyl or tallow pyridinium chloride, tallow pyridinium methyl sulphate and like compounds.

Mixtures of more than one cationic surfactant of the foregoing classes may be employed.

Compositions of the present invention can contain, over and above the wax/perfume particles, any amount of cationic surfactant, for example up to 60%. Preferred compositions have less than 20%, preferably 0.1% to 10%, especially 1% to 8%.

Optional Components

In addition to the cationic surfactant, the basic composition of the present invention into which the particles are incorporated can contain various optional components. These can vary with the nature of the basic composition and can include non-cationic surfactants, detergency builder salts, nonionic softeners, etc. In the preferred fabric-softening compositions of the present invention, the main active ingredient is a di-higher alkyl quaternary ammonium softener in aqueous solution. However, nonionic softeners are advantageously included, for example the materials described in German Offenlegungsschrift No. 26 31 114. These materials, as hereinbefore indicated, are also useful as the carrier substance for the particles of the present invention.

Other ingredients employable in fabric softening compositions can also be included, for example ironing aids such as silicones or dextrin derivatives, preservatives, bactericides, whether effective to protect the composition or to treat fabrics, viscosity controllers, coloring materials and the like.

The textile conditioning compositions according to the invention may be in any physical form, such as liquid, which is the most usual for for such compositions, pastes, gels, granular solids or briquettes, or they may be releasably associated with a soluble or insoluble rigid or flexible solid substrate. The amounts of the components in the compositions will of course depend upon the physical form and upon the amount of the composition intended to be used in the treatment bath, so as to supply the required concentration of its active components. In every case, it is of course essential that the wax/perfume particles are present, in particulate form, in the bulk of the composition which, essentially, contains a cationic fabric-substantive surfactant.

The compositions of the present invention contain, by weight of the composition, from 0.1% to 20% of the wax/perfume particles. Preferred compositions have from 0.5% to 10%, especially from 1% to 5%.

Although fabric softening compositions are highly preferred embodiments of the present invention, other types of products utilizing the wax/perfume particles are possible, for example hair conditioners.

In preparing the compositions, it is necessary to prepare the mixture constituting the particles, and to disperse it in or on the rest of the composition in the form of finely divided solid particles. This can be done in an effective way. For instance if the composition is to be liquid, the components of the particles may be melted together, chilled and solidified in the form of chips, ribbons or particles, and these may be ground in a mill such as a colloid mill in the presence of the rest of the liquid composition. In this case the size reduction and dispersion are performed in a single operation. Alternatively, the melt may be solidified and ground and the fine particles mixed into a solid or liquid or paste carrier medium, which may constitute part or the whole of the remainder of the intended finished composition. Cryogenic grinding, as in the presence of liquid nitrogen, may be appropriate in some instances.

The following examples are illustrative of the present invention.

EXAMPLE 1

A particle mixture was prepared by melting together at about 115° C. 3 parts by weight of Veba SP 1044 wax (Trade name of Veba Chemie AG—melting point 106°–111° C.) and 1 part of a blend of perfume raw materials which is widely used in marketed textile softening products. This was a perfume blend intended to be long lasting on fabrics and had boiling temperature above 100° C. The melt was cooled to provide a solid mass which was broken into small pieces. The melting point was 85°–95° C.

A textile treatment composition was then prepared consisting of 6% by weight ditallowyl dimethyl ammonium chloride (DTDMAC), 92.6% water and 1.4% of said wax/perfume mix. The composition was prepared by forming an emulsion of DTDMAC and water, adding said wax/perfume mix in small pieces and passing the whole at about 20° C. through a colloid mill (Premier Colloid Mill B84 made by Premier Colloid Mills Ltd., Walton-on-Thames, England), set so as to reduce the pieces to particles of linear dimension about 50 microns.

Fabrics steeped in an aqueous dispersion (concentration 0.15% by weight) of this composition were more strongly perfumed before and after drying and gave greater perfume impact during ironing than fabrics treated similarly in a composition comprising the same amounts of DTDMAC and perfume alone.

Substantially similar performance is obtained if the Veba Wax is replaced by beeswax; carnauba wax; Shell's Microcrystalline wax 160/185, or Microcrystalline wax 185/190 (m.pt. 160°/185° F. and 185°/190° F. respectively); Mobil wax 2305, Mobil wax 2360, octadecanol, eicosanol, tallow alcohol, palmitic, stearic, or behenic acid, hardened tallow fatty acid or castor wax. Similar results were obtained when the Veba wax was replaced by Witcodur 263 or 273, Witcotack 143 or 145 or Witcovar 146 (Trade Names).

EXAMPLE 2

A particle mixture was prepared by melting together at about 115° C. 3 parts by weight of Veba SP 1044 wax and 1 part of DTDMAC, and thereafter melting together at about 115° C. 3 parts of this mix with 1 part of the same perfume blend as employed in Example 1. The melt was cooled to a solid mass and broken into pieces. Their melting point was about 80° C.

A textile treatment composition was prepared as in Example 1 but containing the present wax/DTDMAC/perfume particles. The whole mixture was passed through the colloid mill set so as to reduce the particles to linear dimensions in the range about 5 to 50 microns.

Fabrics treated as in Example 1 with this composition were more perfumed and gave even greater impact during ironing than those treated as in Example 1.

In the wax/perfume particles and/or in the composition the DTDMAC is replaced by an equal weight of ditallowyl-dimethyl ammonium methosulphate, N-tallow-N,N,N',N',N'-pentamethyl-1,3-propylenediamine dihydro chloride (Duoquad, Trade name), a ditallow imidazoline softener(Varisoft 455 or 475 Trade name), or N-tallow-N,N',N'-triethanol-1,3-propylenediamine hydrochloride (Dinoramox XH3 - Trade name) with substantially similar effect.

EXAMPLE 3

A composition is prepared containing by weight 3% DTDMAC, 1.5% silicone (polymethyl siloxane having viscosity about 4000 c.s. at 25° C.), 1.5% glycerine monostearate, 1.4% wax/DTDMAC/perfume particles of composition as in Example 2. The composition is prepared by melting together at about 80° C. the DTDMAC and the glycerine monostearate, mixing them into warm water to form an emulsion, adding the silicone, itself in the form of an emulsion prepared in the presence of a cationic emulsifier as described in our above mentioned pending British Pat. application 23171/76, and finally adding the pre-ground wax/DTDMAC/perfume particles. These last are prepared by cryogenically grinding the solid wax/DTDMAC/perfume mix to a particle size of about 100 microns. Fabrics treated as in Example 1 with this composition have improved perfume impact during ironing.

In this composition the DTDMAC may be replaced by an equal amount of dodecyl trimethyl bromide, cetyl trimethyl bromide, cetyl pyridinium chloride, N-tallow propylene diamine dihydrochloride (Dinoramac Trade name), or a polyethyleneimine chloride containing 10 ethyleneimine units, or by a 50/50 mixture of DTDMAC and dodecyl trimethyl ammonium chloride.

EXAMPLE 4

A concentrated liquid textile treatment composition comprises
6% DTDMAC
3% silicone (viscosity 2000 c.s.) as in Example 3
3% Cationic British Gum (British Gum—molecular weight about 5000, reacted with

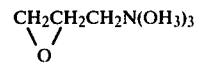

to a degree of substitution of 0.2)
2% wax/perfume/imidazolinium particles prepared as described in Example 2, in small pieces (melting point about 80° C.)
Balance water The mixture is passed through a colloid mill (Premier Colloid Mill as in Example 1) set so as to reduce the particle size to about 20 microns.

The composition makes fabrics treated therewith softer and easier to iron, and provides improved perfume impact during ironing.

EXAMPLE 5

A composition is prepared as in Example 2 wherein the particle mixture comprises by weight 85 parts by weight Shell Microcrystalline 160/185, melting point 160° to 185° F., 5 parts DTDMAC, 10 parts of a blend of perfume oils. The melting point of the mixture is about 60° C.

Fabrics steeped in a dilute solution of this composition have improved perfume impact when dried and during ironing.

EXAMPLE 6

An effective textile softening composition is prepared which comprises, by weight
3 parts DTDMAC
3 parts glycerine monostearate
2 parts N-tallow-N,N',N'-triethanol-1,3-propylene diamine hydrochloride
2 parts silicone (viscosity 4000 centistokes, prepared by polymerising dimethyl siloxane in the presence of DTDMAC)
1 part wax/DTDMAC/perfume particles of Example 2 Balance to 100 - Water The composition is prepared by melting together at 100° C. the DTDMAC and diamine salt, and melting the glycerine monostearate and mixing these into the water, then mixing in the silicone emulsion to form an emulsion. To this is added the solid wax/perfume mixture, and the whole is passed through a Premier Colloid Mill set so as to reduce the particle size of the wax/perfume mixture to less than 100 microns.

EXAMPLE 7

57 parts by weight of DTDMAC and 43 parts by weight of tallow alcohol are melted together at 80° C., cooled and allowed to solidify and then formed into granules by rubbing through a 20 mesh Tyler sieve and collecting the fraction passing a 35 mesh Tyler sieve and retained by a 65 mesh Tyler sieve.

90 parts by weight of these particles are mixed with 10 parts by weight of spray-cooled particles formed from a melt comprising by weight 68% Veba SP 1044 wax, 7% DTDMAC and 25% perfume oil. The melt is spraycooled through a fine pressure-atomising nozzle so as to provide particles of size less than 100 microns.

The resulting granular product constitutes an effective rinse added textile softening and antistatic composition, and provides excellent perfume impact during ironing of treated fabrics.

EXAMPLE 8

A pasty textile conditioning composition comprises
12% DTDMAC
4% particles of composition by weight
 76% glycerine monostearate
 7% cetyl trimethyl ammonium chloride
 10% montmorillonite clay ("Soft Clark" of Georgia Kaoline Co.)
 7% perfume oil
Balance water The particles are prepared by forming a molten slurry of the components and cooling to solidify it. Particles of the solid are cryogenically ground to particle size about 100 microns, and mixed with strong agitation into a paste comprising the DTDMAC and water.

When added at a concentration of about 0.1% to a rinse liquor, this composition provides textile softening and improved perfume impact during ironing and during subsequent storage or use of the fabrics.

EXAMPLE 9

A liquid textile softening composition comprises, by weight, 3% cetyltrimethyl ammonium chloride, 3% ditallow dimethyl ammonium chloride (DTDMAC) and 3% of particles comprising, by weight of the particles, 93% waxy material (Tallow alcohol), 3% DTDMAC, and 4% perfume oil. An emulsion in water is made of the first two components and fine particles mixed into it with strong agitation at room temperature. The fine particles are prepared by forming a melt of the tallow alcohol, DTDMAC and perfume at about 80° C., solidifying it and cryogenically grinding the solid to particle size about 75 microns.

The product has textile softening properties when added to a rinse liquor and provides improved perfume.

EXAMPLE 10

A dispersion of textile conditioning agents is made comprising
 6% DTDMAC
 6% cetyltrimethyl ammonium chloride
 2% particles
all dispersed in 86% water at about 20° C.

The particles comprise 2.25 parts by weight Veba SP 1044 wax (as in Example 1), 0.75 parts perfume oil, and 1 part imidazolinium softener (Varisoft 455), and are prepared by melting these components together at about 100° C. cooling the mix to solidify it, and cryogenically grinding the solid to particle size about 75 microns. The melting point of the particles is about 80° C.

A 9 inch×11 inch substrate sheet is prepared from a roll of randomly laid regenerated cellulose fibres of gauge 3 denier, bonded with a polyvinyl acetate binder (70% cellulose, 30% binder solids) and having a basic weight of 3.8 grs/sheet. The substrate is impregnated by immersion in the above dispersion and surplus dispersion removed by passing the sheet between a pair of rolls. The sheet is then cooled, dried in warm air (at about 35° C.) and weighed and found to have a loading of 3.0 grs/sheet ie. a conditioning agent to substrate weight ratio of 1:1.3.

One such sheet is added to the final rinse (30 liters) in a washing process, providing a concentration of 0.01% conditioning agents. The treated fabrics are softened and provide improved perfume impact.

EXAMPLE 11

A cream hair rinse composition comprises
 3% glycerine monostearate
 6% cetyl dimethyl benzyl ammonium chloride (50% solution)
 1.4% wax/perfume/DTDMAC particles as described in Example 2.
Balance water

EXAMPLE 12

A fabric softening composition is prepared as follows: 2.3 parts by weight of DTDMAC, 3 parts glycerol monostearate and 1.2 parts N-tallow-N,N',N'-triethanol-1,3-propylene diamine hydrochloride are melted together at 70° C. Some, viz. 90% by weight, of this melt is mixed, with vigorous agitation, into 93.5 parts of warm water and the mixture cooled to room temperature. The remaining 10% of the melt is mixed with 0.2 parts by weight of perfume oil and cooled to solidify. The solid is cryogenically ground to form particles of linear dimension about 100 microns, and these particles are mixed into the above mentioned cooled mixture. The product so made has textile softening properties when added to a rinse liquor, and fabrics treated thereby have improved perfume impact.

What is claimed is:

1. A perfumed conditioning composition in the form of an aqueous dispersion and consisting essentially of:
 (i) from 0.1% to 10% of a fabric-substantive cationic surfactant and, in addition,
 (ii) from 0.1% to 20% of particles having an average particle size from 0.1 to 200 microns and a melting point of from 38° C. to 150° C., said particles comprising, by weight of the particles, (a) less than 95% and at least 25% of a carrier substance and (b) from 1% to 75% of a perfume.

2. A composition according to claim 1 consisting essentially of from 1% to 8% of said cationic surfactant and from 1% to 5% of said particles.

3. A composition according to claim 2 wherein said particles have a size in the range from 10 to 50 microns.

4. A composition according to claim 2 wherein said particles have a melting point in the range from 65° C. to 100° C.

5. A composition according to claim 2 wherein said carrier substance is selected from macro- and microcrystalline hydrocarbon waxes, ester waxes having a saponification value not exceeding 100, hydrogenated fats, fatty acids and fatty acid esters of mono- or polyhydric alcohols or anhydrides thereof having from 1 to 8 carbon atoms.

6. A composition according to claim 2 wherein the fabric substantive cationic surfactant is selected from the group consisting of:
 (i) non-cyclic quaternary ammonium salts having at least one $C_{12-30}$ alkyl chain,
 (ii) substituted polyamine salts of formula

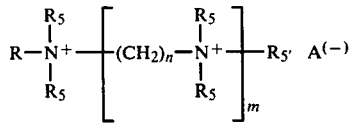

wherein R is an alkyl or alkenyl group having 10 to 22 carbon atoms, the $R_5$'s which may be the same or different each represent hydrogen, a $(C_2H_4O)_pH$ or $(C_3H_6O)_qH$, or a $C_{1-3}$ alkyl group, where each of p and q may be 0 or a number such that (p+q) does not exceed 25, m is from 1 to 9, n is from 2 to 6, and $A^{(-)}$ represents one or more anions having total charge balancing that of the nitrogen atoms, (iii) $C_{8-25}$ alkyl imidazolinium salts, (iv) $C_{12-20}$ alkyl pyridinium salts, and (v) mixtures thereof.

7. A composition according to claim 6 wherein the cationic surfactant is a non-cyclic quaternary ammonium salt having two $C_{12}$–$C_{22}$ alkyl chains and two $C_1$–$C_4$ alkyl chains.

8. A composition according to claim 1 wherein the said particles additionally comprise from 10% to 50% of a fabric-substantive cationic surfactant.

9. A composition according to claim 8 wherein the cationic surfactant present in said particles is selected from the group consisting of:

(i) non-cyclic quaternary ammonium salts having at least one $C_{12-30}$ alkyl chain, (ii) substituted polyamine salts of formula

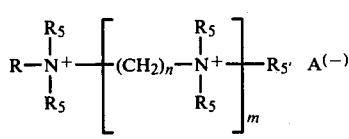 (I)

wherein R is an alkyl or alkenyl group having 10 to 22 carbon atoms, the $R_5$'s which may be the same or different each represent hydrogen, a $(C_2H_4O)_pH$ or $(C_3H_6O)_qH$, or a $C_{1-3}$ alkyl group, where each of p and q may be 0 or a number such that (p+q) does not exceed 25, m is from 1 to 9, n is from 2 to 6, and $A^{(-)}$ represents one or more anions having total charge balancing that of the nitrogen atoms, (iii) $C_{8-25}$ alkyl imidazolinium salts, (iv) $C_{12-20}$ alkyl pyridinium salts, and (v) mixtures of any of these.

10. A composition according to claim 9 wherein said cationic surfactant is a non-cyclic quaternary ammonium salt having two $C_{12}$–$C_{22}$ alkyl chains and two $C_1$–$C_4$ alkyl chains.

11. A composition according to claim 8 wherein the ratio of carrier substance to cationic surfactant in the particles is at least 3:1.